United States Patent [19]

Evans et al.

[11] Patent Number: 4,859,943
[45] Date of Patent: Aug. 22, 1989

[54] INSPECTION METHOD USING MAGNETIC PARTICLES IN A LIQUID CARRIER IN COMBINATION WITH ELECTRICAL DETECTION MEANS

[75] Inventors: Robert S. Evans; Wayne M. Latham; Thomas Powers, all of Lynchburg; Michael O. Robertson, Hurt, all of Va.

[73] Assignee: The Babcock & Wilcox Company, New Orleans, La.

[21] Appl. No.: 138,888

[22] Filed: Dec. 28, 1987

[51] Int. Cl.[4] .................. G01N 27/84; G01N 27/90; G01R 33/12
[52] U.S. Cl. ..................................... 324/216; 324/228
[58] Field of Search ............................. 324/214–216, 324/228

[56] References Cited

U.S. PATENT DOCUMENTS

| | | | |
|---|---|---|---|
| 3,215,572 | 11/1965 | Papell | 324/216 UX |
| 3,249,861 | 5/1966 | Pevar | 324/216 |
| 3,786,346 | 1/1974 | Lorenzi | 324/216 |
| 4,121,157 | 10/1978 | Weltman et al. | 324/216 |
| 4,361,806 | 11/1982 | Song | 324/216 |
| 4,433,289 | 2/1984 | Mlot-Fijalkowski et al. | 324/216 X |

FOREIGN PATENT DOCUMENTS 0002920 1/1980 Japan .................................. 324/216

OTHER PUBLICATIONS

Alston et al; Colloidal Solution of $Fe_3O_4$ for Locating Magnetic Defects; IBM Tech. Discl. Bull., vol. 22, No. 8B, Jan. 1980, p. 3800.

Primary Examiner—Gerard R. Strecker
Attorney, Agent, or Firm—Vytas R. Matas; Robert J. Edwards; Eric Marich

[57] ABSTRACT

A method for inspecting the surface of a workpiece for the presence of flaws using a ferrofluid as a penetrant which is applied to the surface of the workpiece and then scanning the surface of the workpiece with electrical detection means placed adjacent to the surface for providing responses indicative of the presence of flaws in the surface of the workpiece. If desired, a magnetic field can be used to induce the flow of the ferrofluid into any flaws prior to inspection, and for post-inspection cleanup as well. By the use of a ferrofluid, the sensitivity of the electrical detection means, advantageously of the eddy current type, is enhanced in typical applications, and also allows the use of an eddy current probe to inspect workpieces made of nonconductive and/or nonferromagnetic materials.

20 Claims, 5 Drawing Sheets

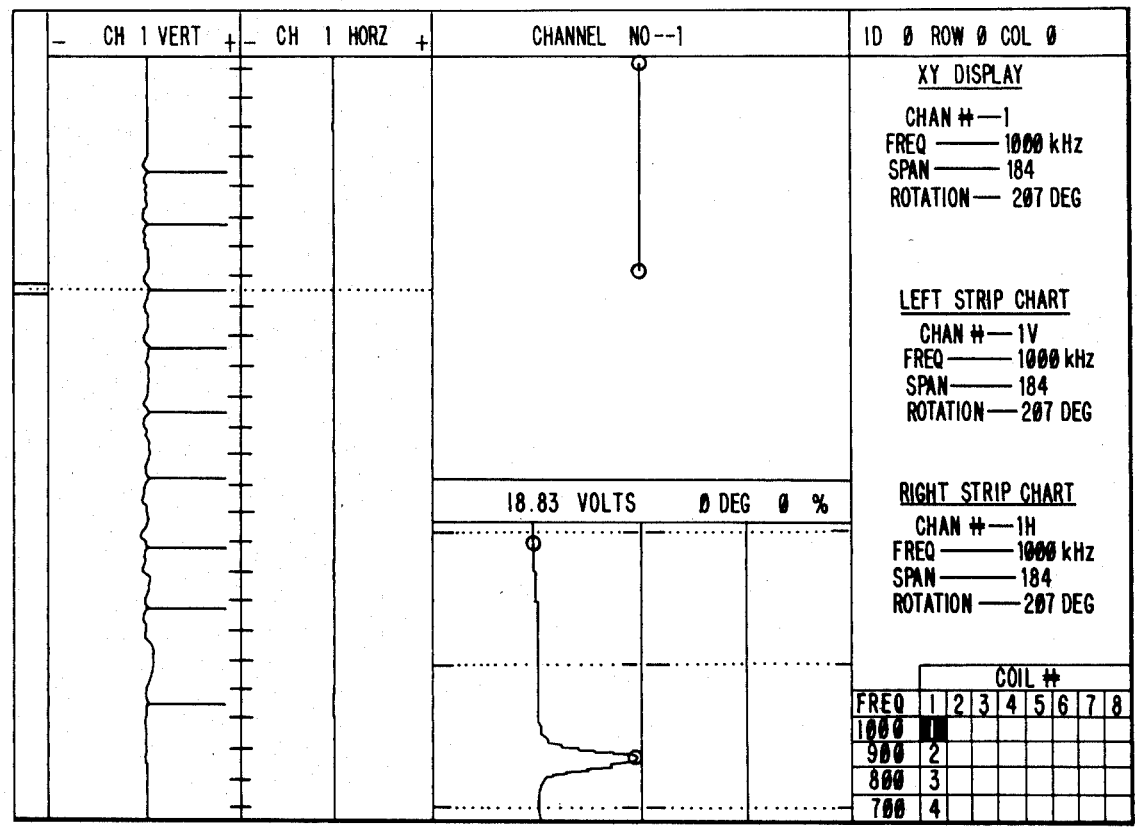
FIG. 5
FIG. 6
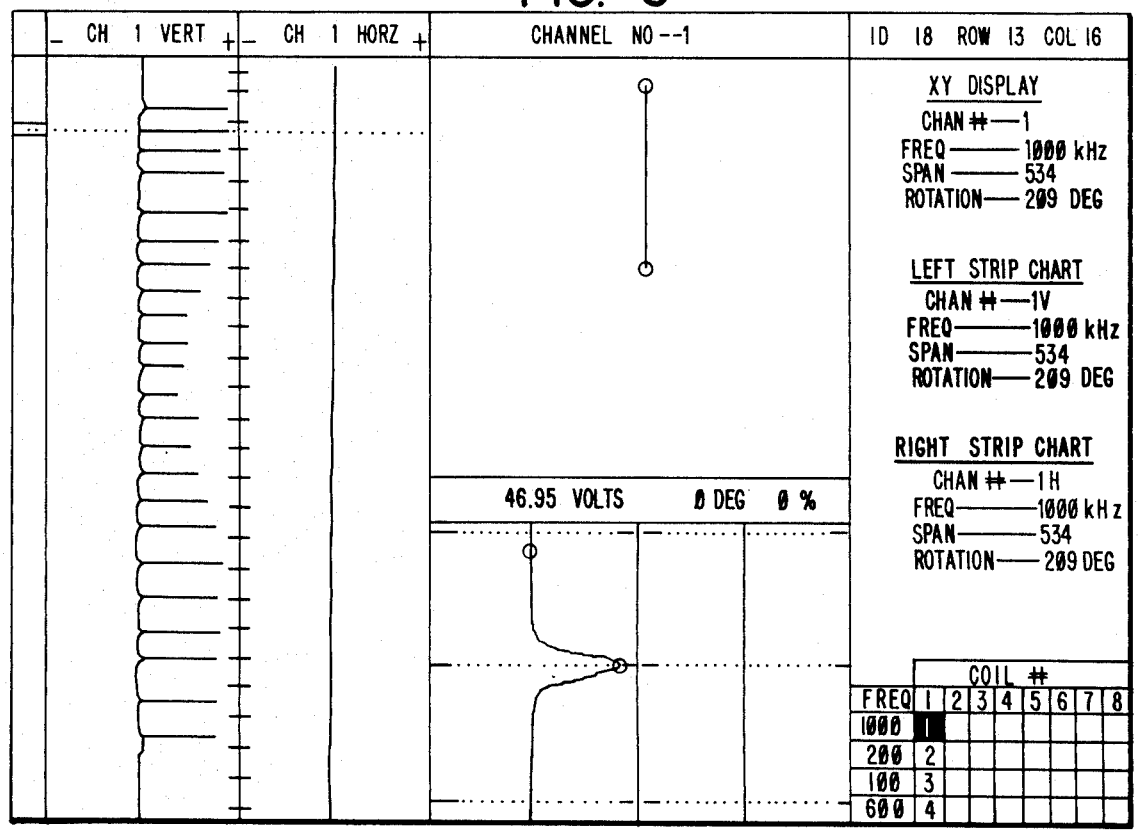

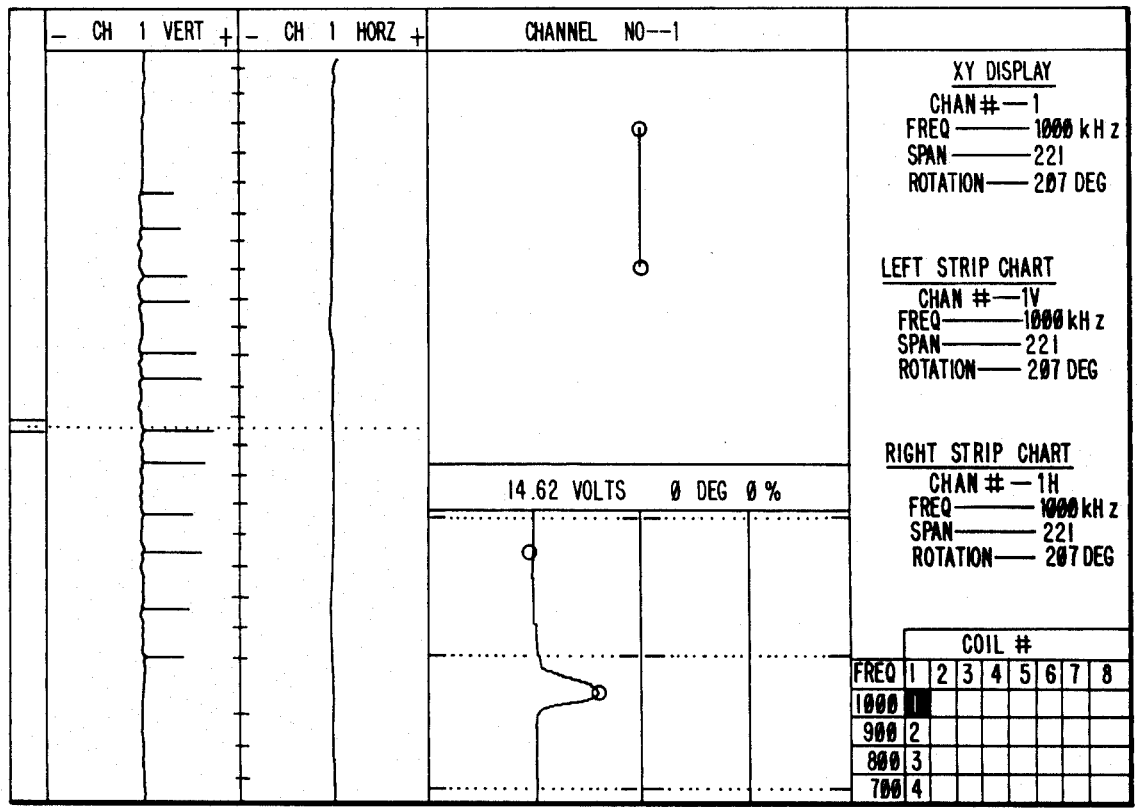
FIG. 7
FIG. 8
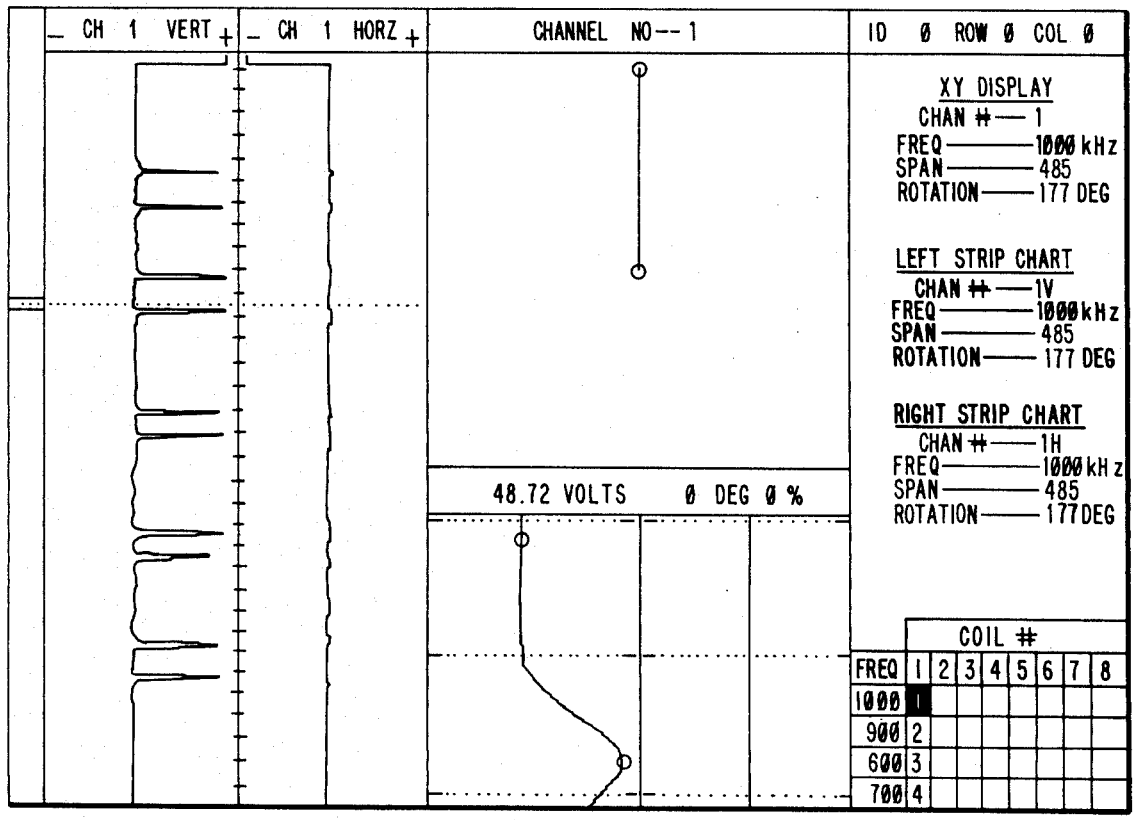

INSPECTION METHOD USING MAGNETIC PARTICLES IN A LIQUID CARRIER IN COMBINATION WITH ELECTRICAL DETECTION MEANS

TECHNICAL FIELD

The present invention relates generally to a method for detecting flaws or discontinuities in the surface of a workpiece and, more particularly, to an inproved flaw detection system which utilizes ferrofluids to penetrate flaws or discontinuities on the surface of the workpiece in conjunction with electrical detection means to scan the surface of the workpiece to detect any flaws.

BACKGROUND ART

Numerous nondestructive testing techniques are available for detecting flaws or discontinuities in the surface of a material. Many of these testing techniques are based on the principle of applying a liquid penetrant (e.g. a dye) over the surface of the material and allowing the dye to penetrate into flaws and discontinuities in the surface of the material by capillary action. These techniques typically require the use of a development agent which is applied over the dye and acts as a blotter to assist the natural seepage of the penetrant out of the flaws or discontinuities within the material. After the surface has been sufficiently "developed", the surface is visually examined for indications of penetrant "bleedback" from surface flaws or discontinuities.

A typical prior art flaw detection technique consists of five basic steps:

(1) surface preparation;
(2) penetration;
(3) removal of excess penetrant;
(4) development; and
(5) inspection.

In the first step, the surface of the material to be inspected is thoroughly cleaned to remove any oil, water or other contaminants from the surface of the workpiece. The resulting cleaned surface is then thoroughly dried. In step 2, the liquid penetrant is applied over the surface of the workpiece and is allowed to remain on the surface for a period of time long enough to allow the penetrant to penetrate into any flaws or discontinuities that are present in the surface. In step 3, any excess penetrant is removed from the surface of the workpiece. The method used to remove the excess penetrant is determined by the type of penetrant used. Some penetrants can be simply wiped off or washed away with water, whereas other penetrants require the use of solvents. In step 4, a thin layer of a powder-like substance is applied to the surface of the material. The powder-like substance acts as a blotter to assist the natural seepage of the penetrant remaining in the surface flaws or discontinuities resulting in a visual indication of the flaw or discontinuity. The final step in this process involves a visual inspection of the surface to detect the flaws or discontinuities made visible by the penetrant and the blotting action of the powder-like substance. The foregoing procedure is very time consuming and relies on the ability of the inspector to detect the surface flaws and discontinuities made visible by the penetrant and the powder-like substance.

Lorenzi (U.S. Pat. No. 3,786,346) discloses a method for detecting defects in a magnetizable test piece using magnetic particles in a viscous fluid. As such, the method disclosed in this reference comprises the steps of spreading a relatively viscous slurry of ferromaganetic flakes over the surface of the test piece, applying a magnetic field to the test piece to orient the ferromagnetic flakes, and inspecting the test piece to determine the existence of flaws within the piece. The application of the magnetic field causes the ferromagnetic flakes adjacent to a flaw to rotate so that their edges are directed toward the viewer causing the flaw to show up as a dark line against a gray background.

Mlot-Fijalkowski, et al (U.S. Pat. No. 4,433,289) discloses a method for testing magnetizable workpiece which comprises the steps of applying a dispersion of ferromagnetic particles in combination with a fluorescent pigment and water soluble carrier on the workpiece to be tested, applying a magnetic field to the workpiece, applying an aqueous spray to the workpiece, drying the workpiece, and examining the workpiece under ultraviolet light.

The above flaw detection techniques have numerous inherent disadvantages in that performance of all the required steps is very time consuming and relies heavily on the visual ability of the inspector to properly examine the material for surface flaws of discontinuities. Furthermore, the techniques of Lorenzi and Mlot-Fijalkowski require magnetizable workpieces.

Additionally, it is known to utilize a ferrofluid (a stable colloidal suspension of sub-domain magnetic particles in a liquid carrier) in determining wall thickness and hole (cooling channel) size in turbine blades in conjunction with an eddy current inspection instrument. It must be recognized, however, that such a technique is drawn to the measurement of relatively large internal features that the user knows are present, in contrast to an inspection of the surface of a workpiece to determine the presence of potentially very "tight" flaws or cracks that may or may not be present.

Because of the foregoing, it has become desirable to develop a flaw detection system which minimizes the amount of time required for the testing procedure and which does not depend upon visual inspection for the detection of surface flaws or discontinuities in the surface of the material.

SUMMARY OF THE INVENTION

The present invention solves the problems associated with the prior art and, through the use of a ferrofluid, the method of the present invention can be used to detect flaws or discontinuities in the surface of nonconductive and/or nonferromagnetic materials.

Accordingly, one aspect of the present invention is drawn to a method for inspecting the surface of a workpiece for the presence of flaws which comprises applying a ferrofluid to the surface of the workpiece and scanning the surface of the workpiece with electrical detection means placed adjacent to the surface of the workpieced for producing responses indicative of the presence of flaws in the surface of the workpiece.

Another aspect of the present invention is drawn to a method for inspecting the surface of a workpiece for the presence of flaws which comprises applying a ferrofluid to the surface of the workpiece, applying a magnetic field to the workpiece to induce the ferrofluid to penetrate into any flaws, and scanning the surface of the workpiece with electrical detection means placed adjacent to the surface of the workpiece for producing responses indicative of the presence of flaws in the surface of the workpiece.

Still another aspect of the present invention is drawn to a method for inspecting the surface of a workpiece for the presence of flaws which comprises applying a ferrofluid to the suface of the workpiece, applying a magnetic field to the workpiece to induce the ferrofluid to penetrate into any flaws, and scanning the surface of the workpiece with an eddy current probe placed adjacent to the surface of the workpiece for producing responses indicative of the presence of flaws in the surface of the workpiece.

The various features of novelty which characterize the invention are pointed out with particularity in the claims annexed to and forming a part of this disclosure. For a better understanding of the present invention and the advantages attained by its use, referenced is made to the accompanying drawings and descriptive matter in which preferred embodiments of the invention are illustrated.

BRIEF DESCRIPTION OF THE DRAWINGS

FIG. 5 is a strip chart recording from an MIZ-18 digital eddy current system showing the response to 600 gauss $M_S$ ferrofluid in a 0.001 inch crack in a Lucite sheet;

FIG. 6 is a strip chart recording from an MIZ-18 digital eddy current system showing the response of 600 gauss $M_S$ ferrofluid in a 0.0025 inch crack in a ceramic block;

FIG. 7 is a strip chart recording from an MIZ-18 digital eddy current system showing the response to a 0.004 inch crack in an aluminum test panel without ferrofluid;

FIG. 8 is a strip chart recording from an MIZ-18 digital eddy current system showing the response to 600 gauss $M_S$ ferrofluid in a 0.004 inch crack in an aluminum panel.

DESCRIPTION OF THE PREFERRED EMBODIMENT

Figure 1:
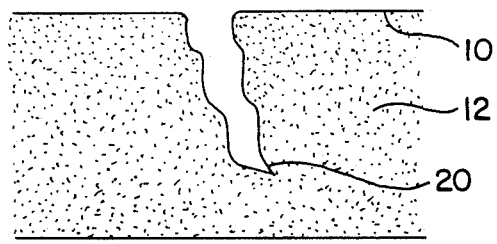
FIG. 1 is a partial cross-sectional view of a workpiece to be inspected having a flaw or discontinuity in the surface thereof.

Referring now to the Figures where the illustrations are for the purpose of describing preferred embodiments of the present invention and are not intended to limit the invention herein, the Figures diagrammatically and/or schematically illustrate the steps involved in the penetrant testing method of the present invention and the results obtained. Like numerals represent the same element throughout the several Figures. The present method utilizes a ferrofluid as the liquid penetrant to determine surface flaws or discontinuities in confunction with electrical detection means.

A ferrofluid can be defined as a stable colloidal suspension of sub-domain magnetic particles ($Fe_3 O_4$) in a liquid carrier. One manufacturer of ferrofluids is Ferrofluidics Corporation, Nashua, N.H., U.S.A. For additional material describing the properties for ferrofluids, the reader is referred to a publication by Ferrofluidics Corporation, Titled "Ferrofluids—Physical Properties and Applications", the text of which is hereby incorporated by reference herein, and a copy of which accompanies the present application.

The two characteristics normally changed in different variations of ferrofluids are the satuation magnetization value ($M_S$) and the type of liquid carrier. The saturation magnetization value $M_S$ is changed solely by increasing or decreasing the volumetric quantity of suspended metallic particles in the colloid. The type of liquid carries available can be characterized as water-based or oil-based. The particles, which have an average size in the range of 100-110 Angstroms ($1*10^{-7}$ mm or $3.937*10^{-9}$ inches), are coated with a stabilizing dispersing agent which prevents particle agglomeration even when a strong magnetic field is applied to the ferrofluid.

In the absence of an external magnetic field, the magnetic moments of the individual particles are randomly distributed and the fluid has no net magnetization. When a magnetic field is applied to a ferrofluid, the magnetic moments of the particles orient along the field lines almost instantly. Thus, the magnetization of the ferrofluid responds immediately to changes in the applied magnetic field. When the applied magnetic field is removed, the moments randomize quickly. Ferrofluids belong to a class of materials known as superparamagnetic materials.

Another property which characterizes a given ferrofluid is its viscosity, which can be varied/specified from less than 5 centipoise to over 25,000 centipoise at 27 degrees C. (80 degrees F.). While the viscosity of a penetrant is relatively unimportant to its penetrability, the viscosity does affect the process. Use of too viscous a penetrant will result in excessive time being required for penetration of a given defect, as well as a potential wastage of penetrant due to excessive "clinging" to the workpiece. Use of a penetrant with too low of a viscosity will result in the penetrant "running" off the workpiece quickly leaving little residue behind for penetrating purposes. Inasmuch as a typical prior art type of red dye penetrant has a viscosity of around 5 centipoise at 100 degrees F., use of a ferrofluid having a viscosity in approximately the same range (less than 5 centipoise at 80 degrees F.) achieves the best results.

Additionally, the viscosity of a ferrofluid is somewhat of a function of the saturation magnetization value $M_S$. For example, a ferrofluid having a saturation magnetization value $M_S$ of, say 600 gauss has a greater viscosity than one having a saturation magnetization value $M_S$ of 200 gauss, simply because the 600 gauss ferrofluid contains an increased volumetric quantity of suspended $Fe_3 O_4$ particles.

Figure 2:
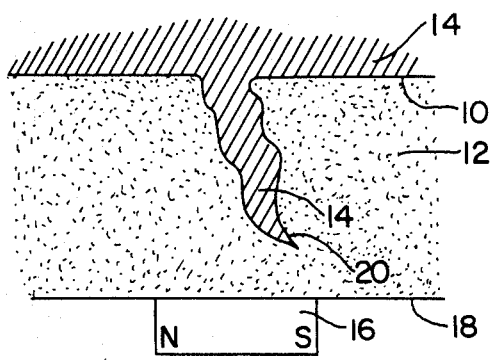
FIG. 2 is a partial cross-sectional view of the workpiece illustrated in FIG. 1, showing the application of a ferrofluid to the surface thereof and the placement of a permanent of electromagnet adjacent to the workpiece to induce flow of the suspension of magnetic particles into the flaws or discontinuities in the surface of the workpiece.
Figure 3:
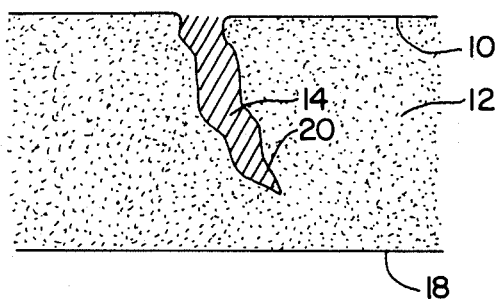
FIG. 3 is a partial cross-sectional view of the workpiece illustrated in FIGS. 1 and 2 showing the remaining ferrofluid within a flaw or crack in the surface of the workpiece after any excess has been removed.
Figure 4:
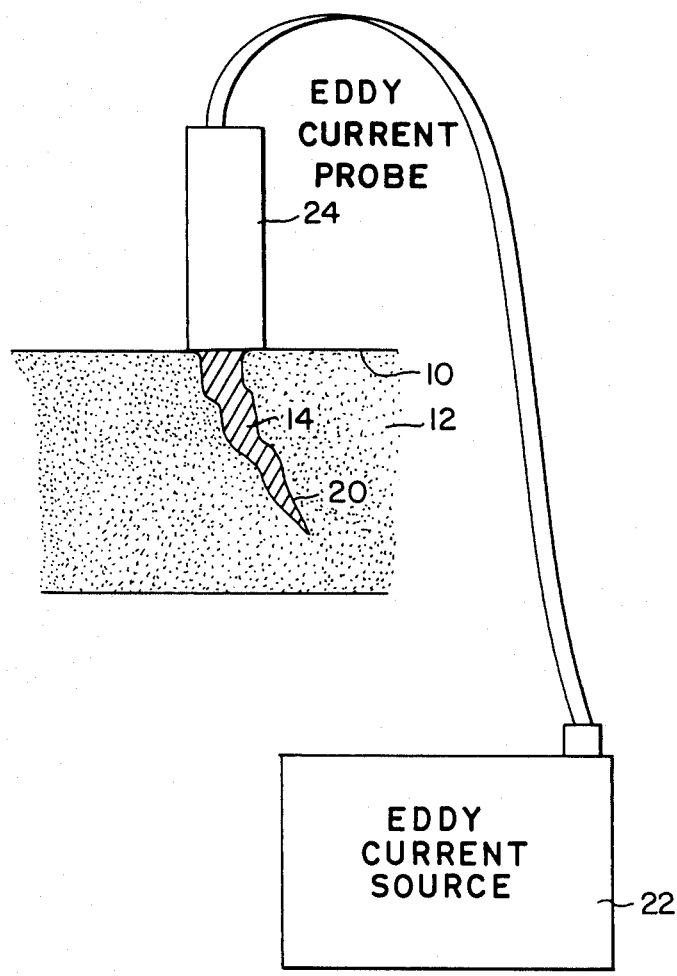
FIG. 4 is a schematic diagram of an eddy current inspection probe apparatus being utilized to detect flaws or discontinuities in the workpiece illustrated in FIGS. 1, 2 and 3 while the ferrofluid is present within a flaw or discontinuity in the surface of the workpiece.

As illustrated in FIG. 1, the surface 10 of the workpiece 12 to be inspected is thoroughly cleaned as in the prior art flaw detection technique previously described. Next, after the surface 10 has been cleaned and thoroughly dried, a ferrofluid 14 is spread over the surface 10 so as to form a film thereon, as shown in FIG. 2. Following removal of the excess ferrofluid 14 from the surface 10 of the workpiece 12, as illustrated in FIG. 3, electrical detection means such as an eddy current source 22 connected to an eddy current probe 24 of known design, such as that disclosed by Lorenzi, et al (U.S. Pat. No. 3,495,166) is utilized to inspect the surface 10 of the material 12 for flaws or discontinuities 20, as shown in FIG. 4. The eddy current probe 24 is allowed to contact the surface 10 of the workpiece 12 and to be moved over same. Any flaws or discontinuities 20 containing the ferrofluid 14 are readily detected by the probe 24 and may be recorded on a recording device, such as a strip chart recorder, etc. (not shown).

To speed up the penetration of the ferrofluid 14 into the flaws or discontinuities 20, and as an additional step in the method of the present invention, a magnetic field may be used depending on test material, wall thickness, etc. The magnetic field, in the form of a permanent or electromagnet 16, can be positioned adjacent to the workpiece 12 but on the side opposite the side on which the ferrofluid 14 has been applied. The permanent or electromagnet 16 induces the flow of the ferrofluid 14 into any flaws or discontinuities 20 in the surface 10 of the workpiece 12. It has been found that the time required for the ferrofluid 14 to enter any flaws or discontinuities 20 in the surface 10 of the workpiece 12 is reduced by orders of magnitude when a permanent or electromagnet 16 is used to induce the ferrofluid 14 into such flaws or discontinuities 20.

For example, tests were performed involving a ⅜" thick aluminum test panel having a 4 inch crack extending completely therethrough, equal 50 ml volumes of conventional red dye penetrant and a 200 gauss oil-based ferrofluid were applied to the test panel over the crack in separate tests. The time for each liquid to completely penetrate through the crack, and hence the ⅜" thick test panel, was measured at approximately one and a half minutes; however, when a magnet was placed on the opposite side of the test panel, the complete penetration of the crack by the ferrofluid took less than one second.

In addition, while the permanent or electromagnet 16 discussed above was shown used to induce penetration of the ferrofluid 14 into surface flaws 20, it can likewise be used, by suitable placement, to induce the ferrofluid 14 to withdraw from the flaws, after the inspection is complete, to clean the workpiece, thereby reducing the time required for post-test cleanup, as well.

In order to compare the method of the present invention to a typical red dye penetrant technique in actual penetrability and detectability, a two-part experiment was conducted in the following fashion:
1. Test objects with discontinuities of known size were tested using the typical red dye penetrant technique, and
2. The same test materials with similar flaws were tested using the method of the present invention.

An MIZ-18 digital eddy current system was utilized as the electrical detection means during the experiment. A specially designed probe employing a small diameter (0.08 inch), radialwound coil was driven at a frequency of 1 MHz in order to provide adequate resolution for the detection of the ferrofluids in the tight cracks. The eddy current test system parameters were set such that the response to the ferrofluids would be completely in the vertical channel. In all cases, the data were collected while scanning the probe head in direct contact with the test specimen.

Three workpieces made of the following materials were used in the experiment:
1. A Lucite plate with a 0.001 inch crack (nonconductor).
2. A ceramic block with a 0.0025 inch crack (nonconductor).
3. An aluminum test panel with a 0.004 inch crack (conductor).

In all cases, the dye penetrant used was a typical Magnaflux red dye penetrant and the ferrofluid was Ferrofluidics Corporation's 600 gauss saturation magnetization ferrofluid in a light mineral oil base.

FIG. 5 shows the graphics display of the eddy current response to the presence of the ferrofluid in the 0.001 inch crack in the Lucite plate when the probe was scanned across the defect. The MIZ-18 graphics printouts seen in FIGS. 5, 6, 7, 8 and 9 show the eddy current responses in several display presentations, pertinent test parameters, signal amplitude in volts, and phase angle in degrees. The two columns on the far left show a typical strip chart presentation of data with both vertical and horizontal signal components. The large window in the upper center portion of the printout contains the Lissajous display representing the X-Y plot of the selected data channel. This section of data and the expanded strip chart presentation below it are selected by the data cursor appearing to the left of the long strip chart display. The graphics printout also documents the test frequency, the span (a number relating to the amplitude of the signal display), and the rotation (a value indicating the angular rotation applied to the raw data).

FIG. 6 shows the eddy current response to the embedded ferrofluid in the ceramic structure. FIGS. 7 and 8 show a comparison of an eddy current inspection of a conductor (the aluminum test panel) with and without the ferrofluid. As expected with a conductor, the mere presence of a crack causes a definite response from the eddy current system (FIG. 7). However, with the addition of the ferrofluid, the response achieved by the probe when scanned across the crack has an increase in signal amplitude by a factor of four (FIG. 8).

As expected, the amplitude of the response of the eddy current system to the ferrofluid is highly dependent upon the saturation magnetization ($M_S$) of the ferrofluid. For instance, compare the graphics display of FIG. 9 (where a 200 gauss saturation magnetization oil-based ferrofluid was placed in the ceramic block crack) to FIG. 6 where the 600 gauss ferrofluid was employed. A significant increase in signal ampitude is shown with the increased saturation magnetization.

It is thus readily apparent that the method of the present invention significantly reduces the time required for inspecting the surface of a workpiece for flaws or discontinuities since it eliminates the need to apply a thin layer of a powder-like substance, as is required in prior art penetrant flaw detection techniques, and to wait until the surface has sufficiently developed. In addition, the present invention eliminates the human factor in detecting such flaws or discontinuities, since it does not depend upon the ability of an inspector to visually detect flaws or discontinuities in the surface of the material. Also, since electrical detection means such as an eddy current device is used in the method of the present invention, a more "permanent" record of the inspection results, by virtue of the capability of the data being recorded and/or the strip charts that can be created, and allows for the inspection process to be adapted to automated inspection schemes.

The use of ferrofluids as the penetrant also provides several inherent advantages in the present invention's penetrant testing techniques. The use of the ferrofluid permits the eddy current inspection apparatus and techniques to be utilized to detect flaws or discontinuities in the surface of not only conductive materials but also in the surface of nonconductive and/or nonferromagnetic materials. The present invention can thus be utilized for the inspection of a wide range of materials including aluminum, ceramics, Incoloy metals, etc. In addition, ferrofluids permit the enhancement of eddy current sensitivity to flaws or discontinuities in the conductive materials. This can be readily seen from an examination of FIGS. 7 and 8.

Figure 9:
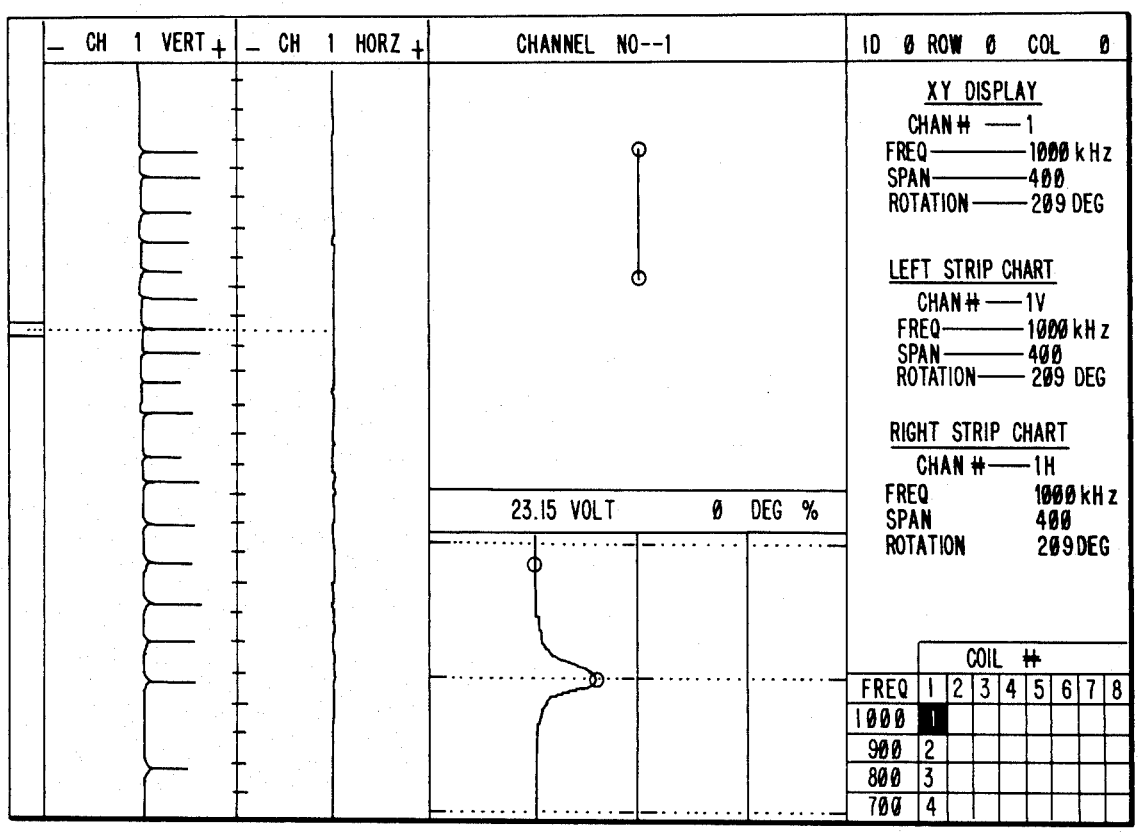
FIG. 9 is a strip chart recording from an MIZ-18 digital eddy current system showing the response to 200 gauss $M_S$ ferrofluid in a 0.0025 inch crack in a ceramic block.

Lastly, variable saturation magnetizations of ferrofluids allow for the custom "tailoring" of eddy current sensitivity to various test materials and flaw characteristics, as shown by a comparison of FIG. 6 with FIG. 9.

Certain modifications and improvements will occur to those skilled in the art upon reading the foregoing. For example, while the term "ferrofluid" has been used throughout the specification, it is understood that any similar suspension of magnetic particles in a liquid carrier will work, provided that its characteristics can be specified and identified as is the case for "ferrofluids", per se. It should be understood that all such modifications and improvements have been deleted herein for the sake of conciseness and readability, but are properly within the scope of the following claims.

We claim:

1. A method for inspecting the surface of a workpiece for the presence of of flaws, comprising:
   applying a ferrofluid to the surface of the workpiece;
   scanning the surface of the workpiece with electrical detection means placed adjacent to the surface of the workpiece for producing responses indicative of the pressence of flaws in the surface of the workpiece; and
   applying a magnetic field to the workpiece to induce the ferrofluid to withdraw from the flaws, after the inspection has been completed, to clean the workpiece.

2. The method as set forth in claim 1 further including the step of cleaning the surface of the workpiece prior to applying the ferrofluid to the surface.

3. The method as set forth in claim 2 further including the step of recording the responses indicative of the presence of flaws.

4. The method as set forth in claim 3 wherein the step of recording the responses indicative of the presence of flaws involves creating a graphical strip chart record.

5. The method as set forth in claim 1 wherein the workpiece is made of ferromagnetic material.

6. The method as set forth in claim 1 wherein the workpiece is made of nonferromagnetic material.

7. The method as set forth in claim 1 wherein the workpiece is made of conductive material.

8. The method as set forth in claim 1 wherein the workpiece is made of non-conductive material.

9. The method as set forth in claim 1 wherein the electrical detection means comprises an eddy current source and probe.

10. A method for inspecting the surface of a workpiece for the presence of flaws, comprising:
    applying a ferrofluid to the surface of the workpiece;
    applying a magnetic field to the workpiece to induce the ferrofluid to penetrate into any flaws; and
    scanning the surface of the workpiece with electrical detection means placed adjacent to the surface of the workpiece for producing responses indicative of the presence of flaws in the surface of the workpiece9

11. The method as set forth in claim 10 further including the step of cleaning the surface of the material prior to applying the ferrofluid to the surface.

12. The method as set forth in claim 10 wherein the magnetic field applied to the workpiece is created by a permanent magnet.

13. The method as set forth in claim 10 wherein the magnetic field applied to the workpiece is created by an electromagnet.

14. The method as set forth in claim 10 wherein the electrical detection means comprises an eddy current source and probe.

15. The method as set forth in claim 10 wherein the applied ferrofluid has a viscosity of less than 5 centipoise at 80 degrees F.

16. A method for inspecting the surface of a workpiece for the presence of flaws, comprising:
    applying a ferrofluid to the surface of the workpiece;
    applying a magnetic field to the workpiece to induce the ferrofluid to penetrate into any flaws; and
    scanning the surface of the workpiece with an eddy current probe placed adjacent to the workpiece for producing responses indicative of the presence of flaws in the surface of the workpiece.

17. The method as set forth in claim 16 further including the step of applying a magnetic field to the workpiece to induce the ferrofluid to withdraw from the flaws, after the inspection has been completed, to clean the workpiece.

18. The method as set forth in claim 17 further including the step of cleaning the surface of the workpiece prior to applying the ferrofluid to the surface.

19. The method as set forth in claim 18 further including the step of recording the responses indicative of the presence of flaws.

20. The method as set forth in claim 16 wherein the step of recording the responses involves creating a graphical strip chart record.

* * * * *